(12) United States Patent
Kim et al.

(10) Patent No.: US 8,280,693 B2
(45) Date of Patent: Oct. 2, 2012

(54) NONDESTRUCTIVE ANALYSIS FOR PERIODIC STRUCTURE

(75) Inventors: Young Dong Kim, Seoul (KR); Jin-Mo Chung, Seoul (KR); Seung-Ho Han, Choongchungnam-do (KR)

(73) Assignee: University-Industry Cooperation Group of Kyung Hee University, Yongin-si, Gyeonggi-do ( * ) Notice: Subject to any disclaimer, the term of this patent is extended or adjusted under 35 U.S.C. 154(b) by 219 days.

(21) Appl. No.: 12/756,980

(22) Filed: Apr. 8, 2010

(65) Prior Publication Data
US 2011/0029286 A1 Feb. 3, 2011

(30) Foreign Application Priority Data

Jul. 30, 2009 (KR) .................. 10-2009-0070308
Feb. 2, 2010 (KR) .................. 10-2010-0009753

(51) Int. Cl.
*H03F 11/24* (2006.01)
*G01B 11/24* (2006.01)
*G01N 21/55* (2006.01)

(52) U.S. Cl. .......... 702/189; 356/601; 356/445
(58) Field of Classification Search ............ 702/189, 702/159, 172; 356/601, 445
See application file for complete search history.

(56) References Cited

U.S. PATENT DOCUMENTS
2008/0297770 A1* 12/2008 Kim et al. .......... 356/73

FOREIGN PATENT DOCUMENTS
KR 10-0892486 4/2009
* cited by examiner

*Primary Examiner* — Michael Nghiem
*Assistant Examiner* — Manuel Rivera Vargas
(74) *Attorney, Agent, or Firm* — Renaissance IP Law Group LLP

(57) ABSTRACT

There is provided a nondestructive analysis for a periodic structure. In the method, a virtual periodic structure is set and divided into a plurality of layers. By utilizing the Lippmann-Schwinger equation with an M-th order interpolation, physical properties related to reflectivity or transmittance of the virtual periodic structure are calculated. An M-th order interpolation formula employed in discretization of the Lippmann-Schwinger equation leads to an accurate and rapid calculation of the physical properties of the periodic structure.

9 Claims, 11 Drawing Sheets

NONDESTRUCTIVE ANALYSIS FOR PERIODIC STRUCTURE

CROSS-REFERENCE TO RELATED APPLICATIONS

This application claims priority and the benefit of Korean Patent Applications No. 10-2009-0070308 filed on Jul. 30, 2009 and No. 10-2010-0009753 filed on Feb. 2, 2010 in the Korean Intellectual Property Office, the entire contents of which are incorporated herein by reference.

BACKGROUND OF THE INVENTION

1. Technical Field

The present invention described herein relates to an analysis method for a periodic structure, the method exemplarily performed through non-destructive testing via measurement of reflectance or transmittance.

2. Discussion of Related Art

Generally, to fabricate electronic devices such as semiconductor devices or display devices, processes of cleaning, thin-film growing, photolithography, and thin-film etching are repeated many times to produce consumer products. For example, in the photolithography process, a circuit of a mask where an image to be fabricated is formed and is transferred to a photosensitive material (photoresist) to form a pattern, and the pattern is used as an etch barrier to form a desired circuit on a thin film.

In semiconductor and display devices fabricated by using the photolithography process, desired circuits need to be transferred to the thin film in an accurate shape in each step. This is possible based on the accuracy of the photolithography process. That is, only when the shape of a desired pattern is accurately transferred to a photoresist and the resist layer properly functions as the etch barrier can an accurate circuit be formed on the thin film. That is, the accurate pattern is to be formed by the photoresist before the circuit is formed on the thin film, and this can be confirmed by a testing process.

To test a pattern, a method of optically observing a shape of a semiconductor device using a pattern tester, for example, has been generally used. However, since the resolution of the pattern tester can be insufficient for determining the shapes of "nano-level" patterns that measure only a few nanometers in length, it is difficult to perform an accurate analysis using a pattern tester. To solve such a drawback, in a semiconductor research and production line, a method of analyzing a specific shape using equipment such as an electron microscope has been used.

However, when an electron microscope is used, since a section of a semiconductor device is cut for shape analysis thereof, the fabricated semiconductor device cannot be used again. Moreover, since the measurement is conducted under a vacuum environment, it can take an excessively long time to obtain a result of the measurement. It may also be impossible to select various regions of a sample to be measured. Due to the aforementioned drawbacks, the electron microscope has a limit in its practical use in the production line.

To address the aforementioned drawbacks, technology using an optical measurement method has been developed and includes, for example, an approximation technique called the Effective Medium Approximation (EMA). A calculation method using EMA has a problem in that, since an approximation is obtained by only a volume ratio of constituent substances in a given period, regardless of a detailed shape of a structure, it never distinguishes a detailed shape of the structure. That is, since the shape of each pattern of a circuit with a periodic structure is not specifically distinguished and only the volume ratio of constituent substances in a given period is distinguished, the difference between the real structure and the measured structure is significant. Specifically, in the periodic structure, since the calculation method using the EMA cannot clarify the different periodic structures if their volume ratios are the same, a new optical measurement method is particularly needed.

SUMMARY

Therefore, in an embodiment of the present invention, a nondestructive testing method is provided that is capable of analyzing a specific shape of a periodic structure and its internal components.

In a particular embodiment of the present invention, a nondestructive analysis for a periodic structure is provided that includes a step of (a) illuminating a real periodic structure and measuring at least one physical property related to reflectivity or transmittance of the real periodic structure in response to the illumination; (b) calculating at least one physical property related to at least one of reflectivity or transmittance of a virtual periodic structure in response to the illumination, by setting the virtual periodic structure having a repeated shape, one-dimensionally, two-dimensionally or three-dimensionally and at least a horizontally repeating period, by dividing the virtual periodic structure into vertically stacked N layers, by defining a zero-th order structure and a perturbed structure from the virtual periodic structure, said perturbed structure being obtained by geometrically or physically changing the zero-th order periodic structure in a perturbation region, by calculating the zero-th order reflected or transmitted wave when light is incident on the zero-th order structure, by discretizing the Lippmann-Schwinger equation using M-th order interpolation ($2 \leq M \leq N$) with at least one divided layer of the virtual periodic structure, by calculating the perturbed reflected or transmitted wave from the discretized Lippmann-Schwinger equation, and by calculating the perturbed reflectivity or transmittance from the zero-th order reflected or transmitted wave and the perturbed reflected or transmitted wave; (c) comparing the at least one physical property related to the reflectivity or the transmittance being measured in the step (a) with the corresponding at least one physical property related to the at least one of reflectivity or transmittance being calculated in the step (b).

In accordance with one embodiment of the present invention, the step (b) further comprises steps of: partitioning the N layers of the virtual periodic structure into X sections ($1 \leq X \leq (N-1)$), and discretizing the Lippmann-Schwinger equation using Mi-th order interpolation ($1 \leq Mi \leq N$) with the partitioned sections.

In accordance with one embodiment of the present invention, at least one of the partitioned sections has different number of layer from other sections.

The reflectivity or transmittance can be that of other detectable diffraction orders as well as the principal order (zero-th order), The surface of virtual periodic structure may have a substance outside the layer, said the substance being a gaseous, liquid, or solid phase, The virtual periodic structure can be allowed to have at least one surface layer, and the surface layer includes at least one of a layer selected from the group consisting of an oxide layer, a coating layer, or a surface roughness layer.

The physical properties may be related to amplitude or phase of a reflected wave or a transmitted wave of an incident wave.

In accordance with one embodiment of the present invention, the step (b) further comprises steps of: expanding perturbation potential in each divided layer in a Fourier series;

and applying the M-th order interpolation formula for the perturbed wave to the reflected or transmitted wave in each divided layer separately according to the layer index.

The virtual periodic structure can be divided into N layers with at least two different heights.

Accordingly, in accordance with a particular embodiment of the present invention, by discretizing the Lippmann-Schwinger equation using M-th order interpolation, an accurate calculation of the physical properties related to the reflectance or transmittance of the virtual periodic structure can be performed more rapidly. Furthermore, microscopic change relative to an original periodic structure having a native oxide layer thereon or an intentionally formed surface coating layer thereon can be precisely tested. The development of the semiconductor industry or other nano-technology can benefit from such embodiment of the invention.

BRIEF DESCRIPTION OF THE DRAWINGS

Features and advantages of embodiments of the present invention will be apparent in accordance with the detailed description of preferred embodiments thereof with reference to the attached drawings, in which.

DETAILED DESCRIPTION

Particular embodiments of the present invention will be described more fully hereinafter with reference to the accompanying drawings. However, the embodiments of the present invention can be achieved with various modifications, and are not limited to the exemplary embodiments described herein.

Figure 1:
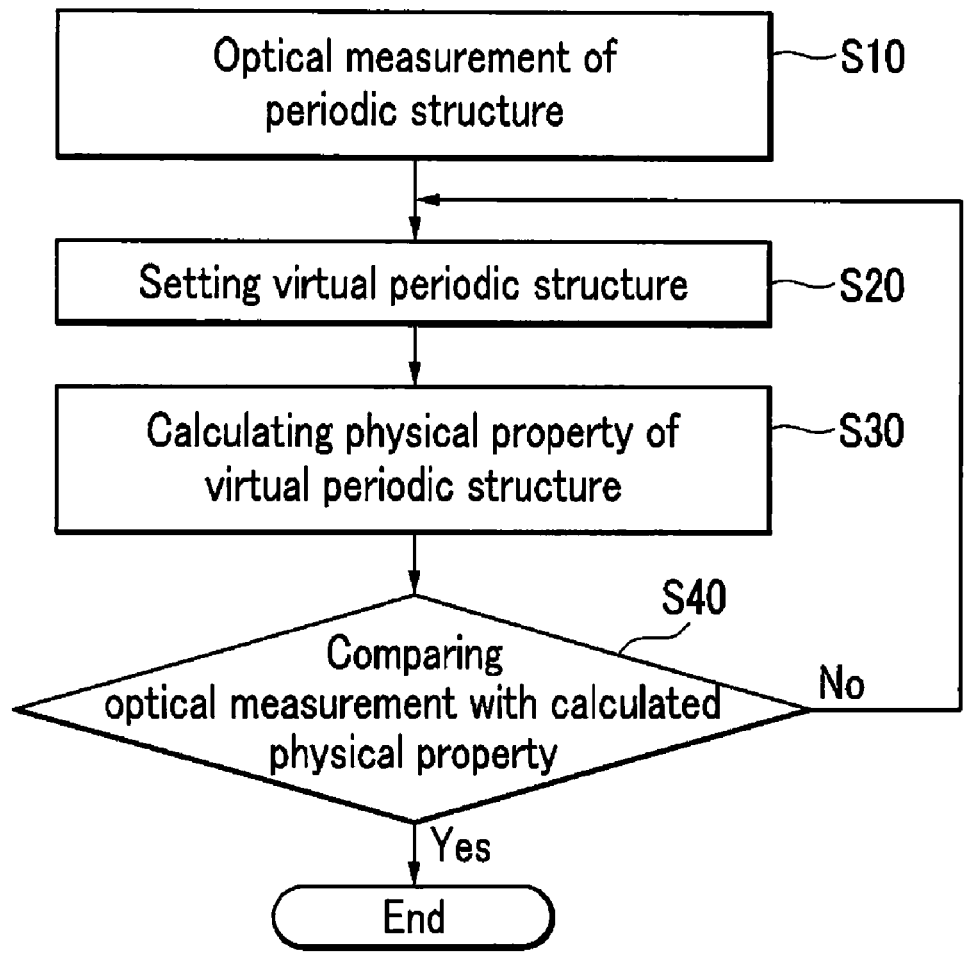
FIG. 1 is a flowchart schematically illustrating a testing method according to an embodiment of the present invention.
Figure 2:
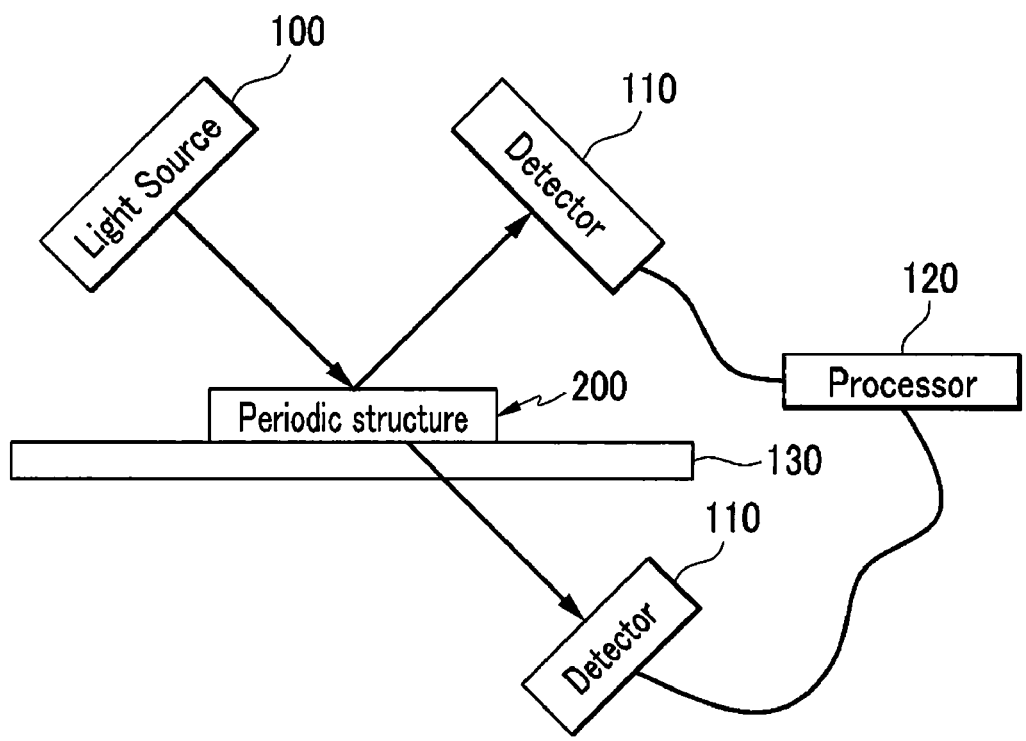
FIGS. 2 and 3 are block diagrams schematically illustrating testing devices of a periodic structure.
Figure 3:
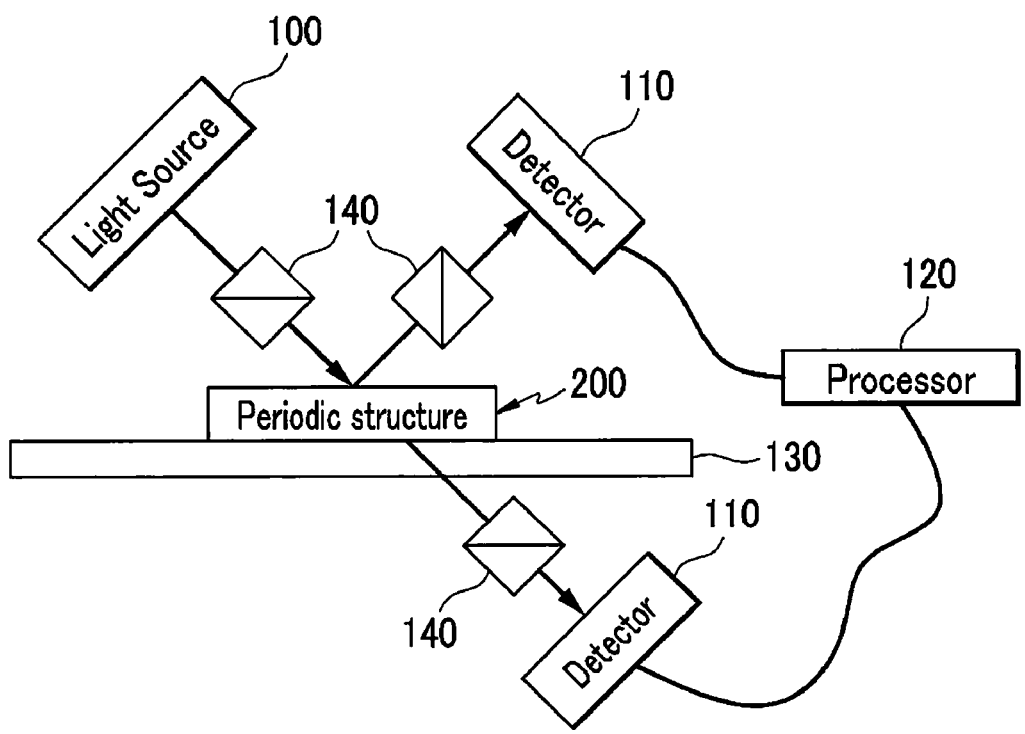

First, through FIGS. 1 to 3, an overall procedure of testing a periodic structure in accordance with an embodiment of the present invention is illustrated.

FIG. 1 is a flowchart schematically illustrating a testing method according to an embodiment of the present invention, and FIGS. 2 and 3 are block diagrams schematically illustrating testing devices for a periodic structure.

In accordance with a particular embodiment of the present invention, a nondestructive testing method includes a step of measuring optical properties by illuminating a real periodic structure (S10), a step of setting a virtual periodic structure (S20), and a step of calculating physical properties of the virtual periodic structure (S30), and a step of comparing the measured physical properties and the calculated physical properties (S40). Each step is described in more detail as follows.

Measurement of Periodic Structure

First, optical properties are extracted from the measured reflectance or transmittance by illuminating a real periodic structure to be tested (S10). The reflectance (R) is measured when a reflecting feature of the periodic structure is dominant, and the transmittance (T) is measured when a transmitting feature is dominant. Step S10 can be performed by use of testing devices as illustrated in FIG. 2 or FIG. 3.

Referring to FIG. 2, the testing devices include a light source (100), a detector (110), a processor (120), and a substrate (130). When a periodic structure as a test object is positioned on a substrate (130), the light source (100) emits light having a specific wavelength or various wavelengths to the periodic structure (200).

The light incident on the periodic structure 200 is partially transmitted and partially reflected. The reflected light is detected in the detector 110, and the reflectance of a reflected wave measured in the detector 110 is calculated in the processor 120. The transmitted light is also detected in the detector 110, and the transmittance of a transmitted wave measured in the detector 110 is calculated in the processor 120.

The testing device may further comprise a polarizer 140 as illustrated in FIG. 3. In this case, the light generated from the light source 100 is polarized as the light of a TE mode or TM mode through the polarizer 140, to be incident on the periodic structure 200. When the light is incident on the periodic structure 200, the incident light is divided into the reflected light and the transmitted light. In an embodiment of the present invention, reflectance or transmittance in the most basic two polarization states in the reflection or transmission of the light, that is, the TE mode and the TM mode, are calculated to perform the nondestructive test of the periodic structure.

For example, the physical properties related to the reflectance or transmittance which is measured by allowing the light to be incident on the periodic structure may be understood as the combination of the physical properties, which are related to an amplitude or phase of a reflected wave and a transmitted wave to an incident wave of a TE mode electric field, and the physical properties, which are related to an amplitude or phase of a reflected wave and a transmitted wave to an incident wave of a TM mode magnetic field. As described above, step S10 can be performed simply by irradiating light on a test object and measuring reflectance or transmittance in the manufacturing process of semiconductor devices. As a consequence, non-destructive measurement of a semiconductor device can be readily performed without changing manufacturing environments.

A virtual object that gives rise to the same calculated reflectance or transmittance as the measured reflectance or transmittance should be established, as the structure of this virtual object will be identified with the periodic structure (200) upon which the optical measurement was performed in step S10. The reflectance or transmittance of the virtual periodic structure is calculated in steps S20 and S30.

To calculate the $\Psi$ and $\Delta$ for a virtual periodic structure, a virtual periodic structure is to be conjectured first in step S20. In general, there is a desired structure when a semiconductor device is manufactured, and a virtual periodic structure is conjectured based on the desired structure.

Virtual Periodic Structure

FIGS. 4 to 8 illustrate examples of virtual periodic structures.

Figure 4:
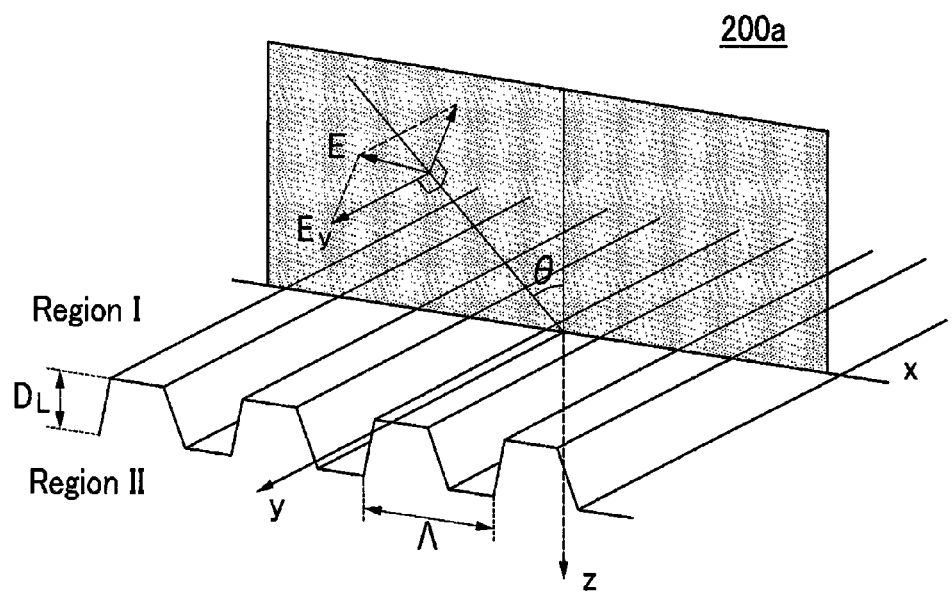
FIG. 4 is a perspective view illustrating an example of a virtual periodic structure.
Figure 5:
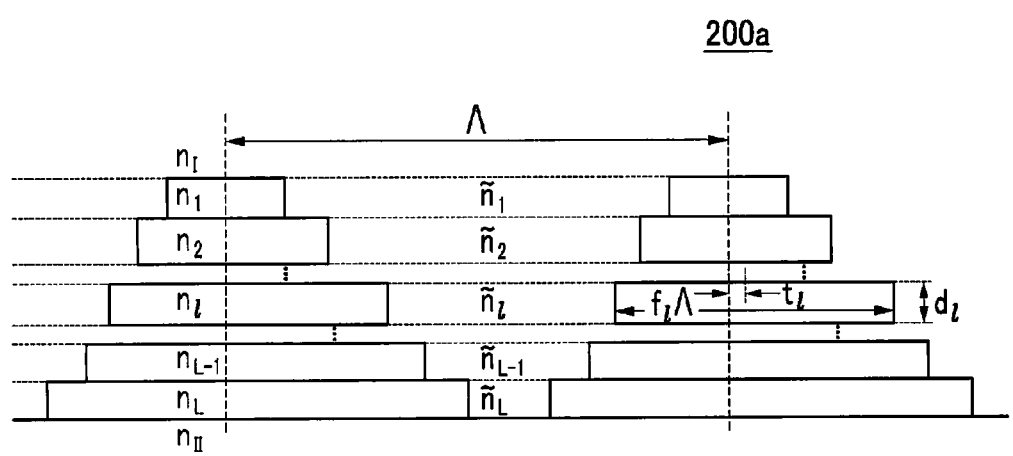
FIG. 5 is a sectional view of the virtual periodic structure of FIG. 4 being divided into a plurality of layers.
Figure 6:
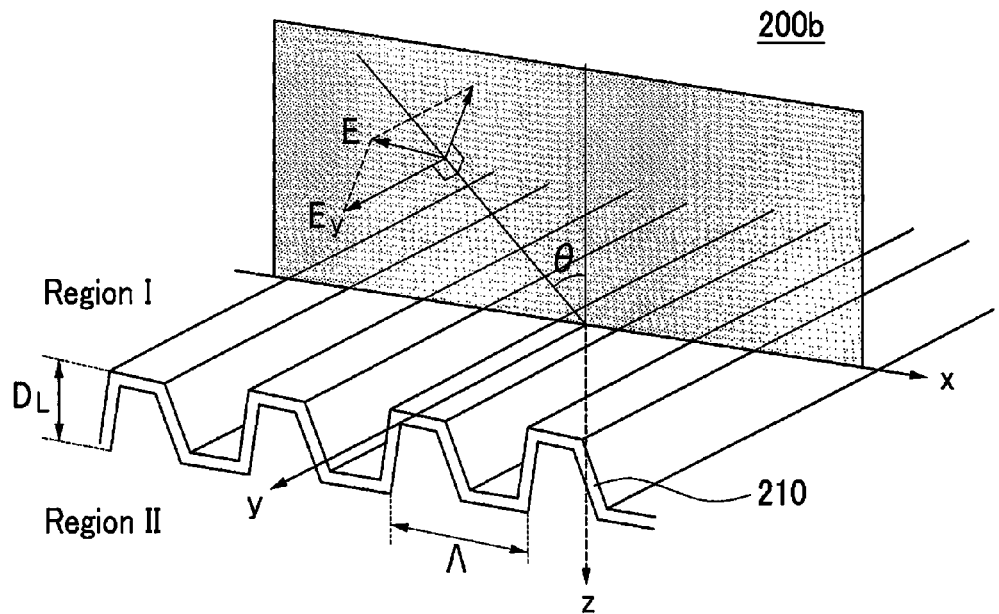
FIG. 6 is a perspective view illustrating another example of a virtual periodic structure.
Figure 7:
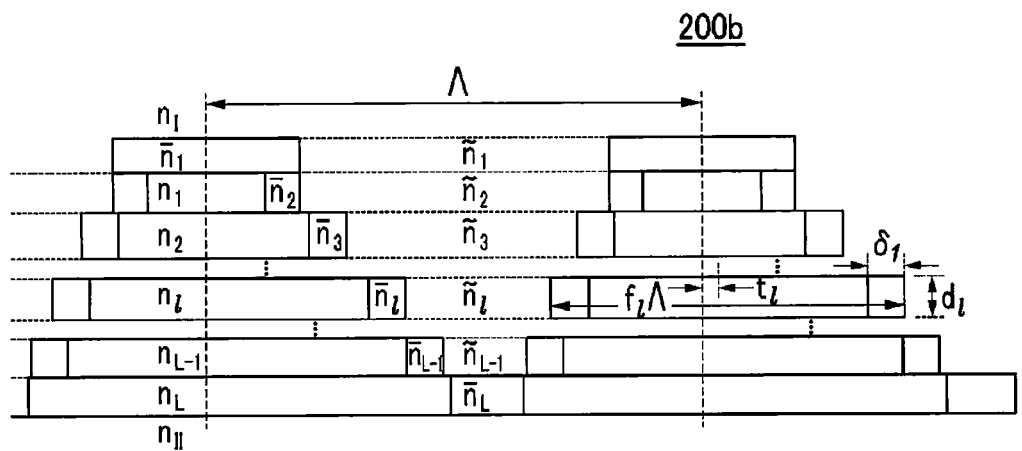
FIG. 7 is a sectional view of the virtual periodic structure of FIG. 6 being divided into a plurality of layers.

FIG. 4 is a perspective view illustrating an example of a virtual periodic structure, FIG. 5 is a sectional view of the virtual periodic structure of FIG. 4 being divided into a plurality of layers (N layers), FIG. 6 is a perspective view illustrating another example of a virtual periodic structure, and FIG. 7 is a sectional view of the virtual periodic structure of FIG. 6 being divided into a plurality of layers.

FIGS. 4 and 5, and FIGS. 6 and 7, illustrate examples of virtual periodic structures. Calculations in step S30 can be performed by (i) dividing the zero-th structure (FIGS. 4 and 5, and FIGS. 6 and 7, are understood to represent the zero-th structure in this case) (200a or 200b) into a plurality of thin layers, (ii) obtaining the functional forms of the projected-space zero-th order reflected or transmitted wave in each layer with two kinds of integration constants, and (iii) fixing the integration constants by the matching conditions at boundary surfaces of the divided layers.

Differently from FIGS. 4 and 5, FIGS. 6 and 7 illustrate an assumed surface layer (210), such as an oxide layer and the like, on the surface of the virtual periodic structure (200b). Because in general, even if a manufacturing process of semiconductors is performed in vacuum a thin surface layer is quickly formed, it can be more desirable to carry out step S30 by taking into account a surface layer (210) as in FIGS. 6 and 7 rather than as in FIGS. 4 and 5.

In a case where the virtual periodic structure (200a) is a semiconductor device having a shape of, for example, one-dimensional, two-dimensional, or three-dimensional periodic formation, the virtual periodic structure (200a) has a formation in which two substances or substance parts (refractive indices from $n_l$ to $n_L$) formed of a substance, such as silicon and the like, in each layer, and substance parts (refractive indices from $\tilde{n}_1$ to $\tilde{n}_1$) of an incident part, such as an air layer and the like, are horizontally periodic.

However, in the real environment of the semiconductor process and the like, since it is impossible to fabricate the periodic structure in a perfect vacuum state, an oxide layer is formed on the surface of the real periodic structure by contact with air or water. Further, in the processing steps, since an intentional coating layer is formed on the surface of the periodic structure or a roughness layer is present on the surface of the periodic structure, the periodic structure of FIG. 4 has a limit in how closely it matches the real geometrical shape thereof.

FIGS. 6 and 7 illustrate a surface layer (210), such as an oxide layer and the like, on the surface of the virtual periodic structure (200b). When a section of the virtual periodic structure (200b) is divided into a plurality of layers, the virtual periodic structure (200b) has the formation in which at least three substances are periodically repeated, as illustrated in FIG. 7. The virtual periodic structure 200b includes a ridge region formed at both sides of a third substance corresponding to a groove region. This ridge region is formed of a first substance forming a center part, and a second substance including the surface layer formed on the outer surface of the center part.

In FIG. 7, $n_l$ (l=2, ..., L), $\tilde{n}_l$ (l=2, ..., L−1), and $\bar{n}_l$(l=1, ..., L) respectively represent the refractive index of the ridge region (the first substance), the groove region (the third substance), and the surface layer region (the second substance).

The surface layer region (the second substance) may be the oxide layer or the coating layer, or it may be the roughness layer of the periodic structure surface as the case may be. A third substance occupying the groove region may be in gaseous, liquid, or solid state, or a combination thereof.

For example, when the virtual periodic structure (200b) is a semiconductor device, a plurality of layers (1 to L) excluding the highest layer (layer 1) can be formed of the first substance being a semiconductor such as silicon and the like, and the highest layer (layer 1) being a second substance such as an oxide layer or a coating layer. A third substance being an air layer or other gas, liquid, or solid state substance can be disposed in grooves between the layers 1 to L. The layers 1 to L and the third substance can be horizontally and periodically repeated within the periodic structure.

When the virtual periodic structure (200b) is set by taking into account the surface layer (210) such as the oxide layer, coating layer, or roughness layer of the surface, the reflectance or transmittance of the virtual periodic structure is calculated to more closely approximate those of the real periodic structure. Consequently, the shape and components of the real periodic structure can be accurately measured. Specifically, it is possible to compare and analyze the geometrical shape and the internal components of the periodic structure, including the thicknesses of thin film structures present within the periodic structure.

From the thus-determined virtual periodic structure, the reflectance or transmittance is obtained by means of calculation (S30). A method for calculation of the reflectance or transmittance will be described later.

In the next step (S40), the reflectance or transmittance calculated in step S30 is compared with the reflectance or transmittance measured in step S10. The actually-measured reflectance or transmittance of a periodic structure or related physical quantities is compared with the calculated reflectance or transmittance of the virtual periodic structure or related physical quantities. When these values are the same within a prescribed error range, the structure of the real periodic structure, as determined from measurements of reflectance or transmittance, can be determined as being identical with that of the virtual periodic structure. When comparing the measured reflectance or transmittance with the calculated reflectance or transmittance, an additional device such as a computer, for example, may be used for comparing the measured value with the calculated value. By this method, geometry, e.g., shape and dimensional aspects of the real structure (200) can be precisely and efficiently determined.

Moreover, the reflected or transmitted wave by a periodic structure has several diffraction orders including the principal order (zero-th order). Usually, the principal order wave is considered, but other orders (1, 2, ..., and −1, −2, ...) should also be considered in a case where the profile of a periodic structure is asymmetric. A particular embodiment of the present invention can be equally applied to reflected or transmitted light of an order other than the principal one.

In the comparison, if both the calculated and measured quantities are the same within a prescribed error range, a testing process is finished since the real periodic structure (200) measured in step S10 is identical with the virtual periodic structure in step S20. On the contrary, if they are not the same, a new reflectance or transmittance is obtained by repeating steps S20 and S30 with the changed optical and geometrical parameters of a virtual periodic structure.

Calculation of Zero-th Order Waves

Following the procedure described above, the process of analyzing a periodic structure utilizing the Green function method is performed.

Calculations that should be carried out in step S30 to obtain the calculated reflectance or transmittance are described below.

In an embodiment of the present invention, to calculate the physical properties of the virtual periodic structure, a shape of another virtual periodic structure with the same period, which will be called a zero-th order structure, is set. Then, the original virtual structure is built by adding a geometrical or physical change, which defines a perturbation potential, to the zero-th order structure in a perturbation domain.

The zero-th order reflected or transmitted wave is calculated first by a rigorous coupled-wave analysis (RCWA) method, then the Lippmann-Schwinger equation is discretized by use of an M-th order interpolation formula ($2 \leq M \leq N$:N is the number of divided layers) for the electric or magnetic field being approximated to a quadratic function with unknown coefficients in each divided layer. By integrating out a series of integrals arising from the discretization, a system of linear equations is produced. From the solutions to this system of linear equations, i.e., the perturbed reflected or transmitted wave, and the zero-th order reflectance or transmittance, the perturbed reflectance or transmittance is extracted. Once the perturbed reflectance or transmittance is obtained, a calculated to reflectance or transmittance of the perturbed structure can be eventually calculated. In this procedure, although a small number of divided layers reduces the computation time, at the same time it reduces the accuracy of the result. Therefore, in order to prevent a reduction of the accuracy for a small number of divided layers, M-th order interpolation can be employed. The M-th order interpolation can be differently applied for each layer or each region (a bundle of layers) divided from the virtual periodic structure. For example, second order interpolation is applied for region (or layer) A, fourth order interpolation is applied for region (or layer) B, and first order interpolation is applied for region (or layer) C. The M-th order interpolation may be varied for each layer or each region according to the shape of virtual periodic structure. As the order of interpolation becomes higher, the accuracy of calculation can be increased by second order at the most. Resultantly, the analysis of the present invention guarantees the accuracy of calculation as well as the reduced computation time for a small number of divided layers.

The N layers divided from the virtual periodic structure can be further partitioned into X sections ($1 \leq X \leq (N-1)$). In this case, the Lippmann-Schwinger equation is discretized by using Mi-th order interpolation ($1 \leq Mi \leq N$:N is the number of divided layers) for the partitioned sections. For example, the N layers may be partitioned into N/2 sections (as a result, the virtual periodic structure is substantially divided into N/2 pair of layers), and then second order interpolation is applied for each section (or each pair). Also, the N layers may be partitioned into N/4 sections, and then fourth order interpolation is used for each section. The N layers can be partitioned into X sections in such a way that each section has different size. That is, at least one of the partitioned sections may have different number of layer from other sections. In this case, the Mi-th order interpolation can be differently applied for the each section having different number of layers.

As described above, the zero-th order reflectance or transmittance can be calculated by the RCWA method. For this purpose, as illustrated in FIGS. 4 to 7, the zero-th order structure (FIGS. 4 to 7 are understood to represent the zero-th structure in this case) (200a or 200b) is divided into a plurality of layers (1 to L) in the thin rectangular sectional shape. Subsequently, the zero-th order dielectric function in each layer is expanded in Fourier series. When light is incident on the zero-th order structure (200a or 200b), the reflected or transmitted wave in each layer is also expanded in Fourier-Floquet series with coefficients, which define a projected-space zero-th wave function (of z) to be determined by matching conditions for electromagnetic waves at the boundary surfaces.

From the aforementioned projected-space zero-th order wave function, the reflectance or the transmittance for a TE mode electric field ($R^{[0]}_{TE}$ and $T^{[0]}_{TE}$) and those for a TM mode magnetic field ($R^{[0]}_{TM}$ and $T^{[0]}_{TM}$) of the zero-th order structure are calculated, and are used in the calculation of the corresponding perturbed values.

More precise solutions can be obtained by increasing the number of layers divided from the virtual periodic structure (200a or 200b) and correspondingly increasing the number of terms of the Fourier series expansion. With the virtual periodic structure (200b) in FIGS. 6 and 7, the method for calculating the perturbed reflectance or transmittance will be described below.

The Green function of the zero-th order structure in the perturbation domain can be obtained by applying the method for calculating the zero-th order reflectance or transmittance. The perturbed reflectance or the transmittance for the TE mode electric field ($R_{TE}$ and $T_{TE}$) and those for the TM mode magnetic field ($R_{TM}$ and $T_{TM}$) can be extracted once the projected-space wave of the TE mode electric field or the TM mode magnetic field in each layer of the virtual structure is calculated by the Lippmann-Schwinger equation.

In accordance with an embodiment of the present invention, the zero-th structure between an incident medium (region I) and a substrate (region II) is divided into L layers, including some or all layers being formed of a uniform substance. There are various possibilities for setting the zero-th structure, among which the following are mentioned: a case where each layer in all layers of the whole perturbation zone is formed of a uniform substance, a case where all layers of the perturbation zone are formed of a single uniform substance, a case where the perturbation zone is placed as the air layer on the substrate, and a case where each layer is not formed of a uniform substance but all layers are formed of one given layer being repeated.

Embodiment

Among the intermediate steps for calculating the reflectance or transmittance of the virtual periodic structure (200b) illustrated in FIGS. 6 and 7, two steps, one for discretizing the Lippmann-Schwinger equation by use of the second-order interpolation and the other for creating a system of linear equations for the discretized projected-space perturbed waves, will be described below.

Below, the calculation will be carried out separately for TE and TM modes. The TE mode case is considered first.

Due to the periodicity of any periodic structure in the x direction, the x-dependence of the TE mode components are completely determined in Fourier-Floquet series:

$$E_y(x,z) = \sum_{n=-\infty}^{\infty} \Psi_n(z) e^{ik_{xn}x}, \quad \text{Eq. (1)}$$

$$H_x(x,z) = i\sqrt{\frac{\varepsilon_0}{\mu_0}} \frac{1}{k_0} \sum_{n=-\infty}^{\infty} \partial_z \Psi_n(z) e^{ik_{xn}x}, \quad \text{Eq. (2)}$$

where $i=\sqrt{-1}$; $k_{xn}=k_0[n_I \sin \theta - n\lambda_0/\Lambda]$; $k_0=2\pi/\lambda_0$ (with $\lambda_0$ being the wavelength of an incident wave in vacuum, $n_I$ being the refractive index of an incident region, and $\theta$ being the incident angle); $\varepsilon_0$ is the permittivity of the vacuum; and $\mu_0$ is the permeability of the vacuum.

The dielectric function of any periodic structure with a one-dimensional period being equal to $\Lambda$ in the x direction can be expanded in Fourier series:

$$\varepsilon(x,z) = \sum_{h=-\infty}^{\infty} \varepsilon_h(z) e^{i2\pi hx/\Lambda}. \quad \text{Eq. (3)}$$

Due to Maxwell's equation, the column vector $\Psi(z)$ (the projected-space wave vector) whose components are the expansion coefficients $\Psi_n(z)$ in Eq. (1) satisfy the following equation:

$$\left[\frac{d^2}{dz^2} + k_0^2 E(z) - K^2\right]\Psi(z) = 0, \quad \text{Eq. (4)}$$

where K is a diagonal matrix with the (n,n) element being equal to $k_{xn}/k_0$ and E(z) is the Toeplitz matrix formed by the permittivity harmonic components, with the (n,p) element being equal to $E_{np}(z)=\varepsilon_{n-p}(z)$.

Below, the Fourier-Floquet space index is truncated so that it runs from $-N$ to $N$. When the periodic structure is set as perturbed structure in which a geometrical or physical change, perturbation potential, is added to zero-th order structure, perturbed dielectric function $\Delta\varepsilon(x,z)$ is defined as $\Delta\varepsilon(x,z)=\varepsilon(x,z)-\varepsilon^{[0]}(x,z)$: $\varepsilon^{[0]}(x,z)$ is dielectric function of the zero-th order structure.

Column vectors $\Psi_l^{[0]}(z)$ and $\Psi_l(z)$ whose components are the expansion coefficient functions (of z) of the zero-th order $E_y^{[0]}(x,z)$ and of the perturbed $E_y(x,z)$ respectively, satisfy the following Lippmann-Schwinger equation:

$$\Psi(z) = \Psi_0(z) + \int G(z,z')V(z')\Psi(z')dz', \quad \text{Eq. (5)}$$

where V(z) is the perturbation potential given by $V(z)=k_0^2[E(z)-E^{[0]}(z)]$ with E(z) and $E^{[0]}(z)$ being the Toeplitz matrices for the virtual periodic structure and the zero-th order structure, respectively. In Eq. (5), since V(z)=0 outside the perturbation domain, the integration region is restricted within the perturbation domain.

In order to solve the Lippmann-Schwinger equation numerically, the $\Psi_l^{[0]}(z)$ and G(z,z') are calculated first by the RCWA method.

Below, the general method for calculating $\Psi_l^{[0]}(z)$ and G(z,z') is described. For a detailed calculation by the RCWA method, refer to Korea Patent No. 10-0892485 and No. 10-0892486.

We approximate the periodic structure, which includes an oxide layer, a coating layer, or a surface layer, to a stack of parallel rectangular layers with a common period $\Lambda$. In the aforementioned division of the periodic structure into layers, some or all the layers may be formed of a uniform substance. By the aforementioned division of the periodic structure into layers, the z dependency of the dielectric function $\varepsilon(x,z)$ is shifted to the index l indicating the layer. Then, the dielectric function of the given layer l is a function of z only and can be expanded in Fourier series since it is still a periodic function in x with a period $\Lambda$. The Toeplitz matrix $E_l^{[0]}$ constructed from the expansion coefficients is of size $(2N+1)\times(2N+1)$. Each column vector $\Psi_l^{[0]}(z)$ of size (2N+1), being constructed from the Fourier-Floquet expansion coefficient functions of the electric field in each layer, satisfies a harmonic-oscillator-type matrix differential equation. Therefore, solving this equation (numerically) amounts to solving the eigenvalue square matrix $Q_l^2$ and eigenvector square matrix $S_l$ (numerically). The application of boundary conditions for $T_l^{[0]}(z)$ and its derivative gives rise to a recurrence relation for two kinds of integration constant matrices. From the special conditions in which there is no incident light from region II (l=L+1) and the incident light from region I (l=0) is known, the projected-space zero-th order wave $\Psi_l^{[0]}(z)$ is completely obtained numerically.

The calculation of G(z,z') can be carried out basically using the RCWA method and can be expressed in terms of the same eigenvalue square matrix $Q_l^2$ and eigenvector square matrix $S_l$ obtained already for the case of $\Psi_l^{[0]}(z)$, and two kinds of constant square matrices $f_{ll'}^{\pm}(z')$ and $g_{ll'}^{\pm}(z')$ as follows:

$$G(z,z') = \quad \text{Eq. (6)}$$

$$\begin{cases} S_l[e^{-Q_l(z-z_{l-1})}f_{ll'}^-(z') + e^{Q_l(z-z_{l-1})}g_{ll'}^-(z')] & (l<l') \\ S_l[e^{-Q_l(z-z_{l-1})}f_{ll'}^-(z') + e^{Q_l(z-z_{l-1})}g_{ll'}^-(z')] & (l=l', z<z') \\ S_l[e^{-Q_l(z-z_{l-1})}f_{ll'}^+(z') + e^{Q_l(z-z_{l-1})}g_{ll'}^+(z')] & (l=l', z>z') \\ S_l[e^{-Q_l(z-z_{l-1})}f_{ll'}^+(z') + e^{Q_l(z-z_{l-1})}g_{ll'}^+(z')] & (l>l'). \end{cases}$$

Differently from the calculation of $\Psi_l^{[0]}(z)$, the source of the Green function is the zero-th order structure itself. Furthermore, in this instance, there is no incident wave from region I. Thus an additional boundary condition for G(z,z') is necessary, which is provided from the discontinuity of the derivative of G(z,z') due to the delta function term. By applying all the boundary conditions, the two constant (in z) square matrices $f_{ll'}^{\pm}(z')$ and $g_{ll'}^{\pm}(z')$ are fixed as follows:

$$f_{ll'}^{\pm}(z') = \overline{T}_{l-1} \ldots \overline{T}_l f_{l'l'}^{\pm}(z'), \quad \text{Eq. (7)}$$

$$g_{ll'}^{\pm}(z') = \overline{t}_{l-1} \ldots \overline{t}_l f_{l'l'}^{\pm}(z'), \quad \text{Eq. (8)}$$

where $$f_{l'l'}^{\pm}(z') = \quad \text{Eq. (9)}$$
$$\frac{1}{2}\left[e^{Q_{l'}(z'-z_{l-1})} + \overline{r}_{l'}u_{l'}\left[R_{l'}e^{Q_{l'}(z'-z_{l-1})} + e^{-Q_{l'}(z'-z_{l-1})}\right]\right]Q_{l'}^{-1}S_{l'}^T,$$

$$g_{l'l'}^{\pm}(z') = \frac{1}{2}u_{l'}\left[\begin{array}{c} R_{l'}e^{Q_{l'}(z'-z_{l-1})} + \\ e^{-Q_{l'}(z'-z_{l-1})} \end{array}\right]Q_{l'}^{-1}S_{l'}^T \quad \text{Eq. (10)}$$

$R_l$ and $\overline{r}_{l'}$ are defined as the square matrices connecting $f_{ll'}^+(z')$ and $g_{ll'}^+(z')$ and $f_{ll'}^-(z')$ and $g_{ll'}^-(z')$: also $u_l$ is defined as $u_l = (I - R_l \vec{r}_l)^{-1}$.

$$g_{ll'}^+(z') = R_l f_{ll'}^+(z') \quad \text{Eq. (11)}$$

$$f_{ll'}^-(z') = \overline{r}_l g_{ll'}^-(z'). \quad \text{Eq. (12)}$$

Below, the method of discretizing the Lippmann-Schwinger equation by use of the $\Psi^{[0]}(z)$ and $G(z,z')$ thus obtained is described.

Discretization of Lippmann-Schwinger Equation with the Second-Order Interpolation Two quantities, $\Psi^{[0]}(z)$ and $G(z,z')$, which are defined by the physical properties and geometrical formation of the zero-th order structure and the information of the incident wave, and the perturbation potential $V(z)$, serve as input functions. By solving the discretized Lippmann-Schwinger equation, an unknown quantity $\Psi(z)$ depending on the physical properties and geometrical formation of the perturbed structure and on the information of the same incident wave is obtained.

It is assumed that the perturbation potential $V(z')$ has a constant value $V_j$ inside layer j. By setting $z \to z_{l-1}$ for z located inside the layer l($l=1, \ldots, L$) and $z \to z_{l-1}$ for z located inside the layer L and by using Eqs. (7) and (8), we transform Eq. (5) as follows:

$$\Psi(z_{l-1}) - \Psi^{[0]}(z_{l-1}) = \qquad \text{Eq. (13)}$$

$$S_l \left[ (1+R_l) \sum_{j=1}^{l-1} \bar{T}_{l-1} \ldots \bar{T}_j \int_{z_{j-1}}^{z_j} dz' f_{jj}^+(z') V_j \Psi(z') + \right.$$

$$(\bar{r}_l + 1) \int_{z_{l-1}}^{z_l} dz' g_{ll}^-(z') V_l \Psi(z') +$$

$$\left. (\bar{r}_l + 1) \sum_{j=l+1}^{L} \bar{t}_l \ldots \bar{t}_{j-1} \int_{z_{j-1}}^{z_j} dz' g_{jj}^-(z') V_j \Psi(z') \right]$$

$$\Psi(z_L) - \Psi^{[0]}(z_L) = \qquad \text{Eq. (14)}$$

$$S_L (e^{-Q_L d_L} + e^{Q_L d_L} R_L) \left[ \sum_{j=1}^{L-1} \bar{T}_{L-1} \ldots \bar{T}_j \int_{z_{j-1}}^{z_j} dz' f_{jj}^+(z') V_j \Psi(z') + \right.$$

$$\left. \int_{z_{L-1}}^{z_L} dz' f_{LL}^+(z') V_L \Psi(z') \right]$$

It is noted that, in Eq. (13), if l=1, $$\sum_{j=1}^{l-1} (\ldots)$$

generates no terms, and if l=L, $$\sum_{j=l+1}^{L} (\ldots)$$

generates no terms.

To enhance accuracy, we carry out analytic integrations within each layer by using the second-order interpolation given in Eqs. (15) to (18); also, M-th order interpolation can be applied.

$$\Psi(z') = \Psi(z_j) + \Psi_A(z_j)(z' - z_j) + \qquad \text{Eq. (15)}$$

$$\frac{1}{2!} \Psi_B(z_j)(z' - z_j)^2 + \frac{1}{3!} \Psi_C(z_j)(z' - z_j)^3 + \ldots$$

In the present embodiment using the second-order interpolation, $\Psi_A$ and $\Psi_B$ can be expanded as follows.

$$\Psi_A = -\frac{d_{j+1}}{d_j(d_j + d_{j+1})} \Psi(z_{j-1}) + \qquad \text{Eq. (16)}$$

$$\frac{d_{j+1} - d_j}{d_j d_{j+1}} \Psi(z_j) + \frac{d_j}{d_{j+1}(d_j + d_{j+1})} \Psi(z_{j+1})$$

$$\Psi_B = 2! \left( \frac{1}{d_j(d_j + d_{j+1})} \Psi(z_{j-1}) - \right. \qquad \text{Eq. (17)}$$

$$\left. \frac{1}{d_j d_{j+1}} \Psi(z_j) + \frac{1}{d_{j+1}(d_j + d_{j+1})} \Psi(z_{j+1}) \right)$$

The z' integrations in Eq. (13) can be carried out separately for even-numbered layers and for odd-numbered layers as in Eq. (16) and Eq. (17), where two layers are paired for the calculation. In the N-th order interpolation, it is considered that N layers should be put in one section. Accordingly, paired layers are considered as one unit in the second order interpolation, and three layers in the third order interpolation, similarly. The aforementioned forms (or equations) can be applied to N-th order interpolation. Eq. (18) and Eq. (19) describe the general integral form for each layer: II indicates even-numbered layers and I indicates odd-numbered layers.

$$\int_{z_{i-1}}^{z_i} dz' f_{ii}^+(z') V_i \Psi_{II}(z') = \qquad \text{Eq. (18)}$$

$$G_i^{(+)} V_i \Psi(z_{i-1}) + G_i^{[A][II](+)} V_i \Psi(z_{i-1}) + G_i^{[B][II](+)} V_i \Psi(z_{i-1})$$

$$\int_{z_{i-1}}^{z_i} dz' f_{ii}^+(z') V_i \Psi_I(z') =$$

$$G_i^{(+)} V_i \Psi(z_i) + G_i^{[A][I](+)} V_i \Psi(z_i) + G_i^{[B][I](+)} V_i \Psi(z_i)$$

$$\int_{z_{i-1}}^{z_i} dz' g_{ii}^-(z') V_i \Psi_{II}(z') = \qquad \text{Eq. (19)}$$

$$G_i^{(-)} V_i \Psi(z_{i-1}) + G_i^{[A][II](-)} V_i \Psi(z_{i-1}) + G_i^{[B][II](-)} V_i \Psi(z_{i-1})$$

$$\int_{z_{i-1}}^{z_i} dz' g_{ii}^-(z') V_i \Psi_I(z') =$$

$$G_i^{(-)} V_i \Psi(z_i) + G_i^{[A][I](-)} V_i \Psi(z_i) + G_i^{[B][I](-)} V_i \Psi(z_i)$$

where $$\begin{pmatrix} G^{(+)} \\ G^{(-)} \end{pmatrix}_i = \begin{bmatrix} (1 + \bar{r}uR)e^{Qd} + \bar{r}u \\ uRe^{Qd} + u \end{bmatrix}_i W_i \qquad \text{Eq. (20)}$$

$$\begin{pmatrix} G^{[A][I](+)} \\ G^{[A][I](-)} \end{pmatrix}_i = -\begin{bmatrix} (1 + \bar{r}uR)e^{Qd} W^{[A](-)} + \bar{r}u W^{[A](+)} \\ uRe^{Qd} W^{[A](-)} + u W^{[A](+)} \end{bmatrix}_i \qquad \text{Eq. (21)}$$

$$\begin{pmatrix} G^{[A][II](+)} \\ G^{[A][II](-)} \end{pmatrix}_i = \begin{bmatrix} (1 + \bar{r}uR)e^{Qd} W^{[A](+)} + \bar{r}u W^{[A](-)} \\ uRe^{Qd} W^{[A](+)} + u W^{[A](-)} \end{bmatrix}_i$$

$$\begin{pmatrix} G^{[B][I](+)} \\ G^{[B][I](-)} \end{pmatrix}_i = -\begin{bmatrix} (1 + \bar{r}uR)e^{Qd} W^{[B](-)} + \bar{r}u W^{[B](+)} \\ uRe^{Qd} W^{[B](-)} + u W^{[B](+)} \end{bmatrix}_i \qquad \text{Eq. (22)}$$

$$\begin{pmatrix} G^{[B][II](+)} \\ G^{[A][II](-)} \end{pmatrix}_i = \begin{bmatrix} (1 + \bar{r}uR)e^{Qd} W^{[B](+)} + \bar{r}u W^{[B](-)} \\ uRe^{Qd} W^{[B](+)} + u W^{[B](-)} \end{bmatrix}_i$$

The quantities $W_i$, $W_i^{[A]\pm}$, $W^{[B]\pm}$ in Eqs. (20) to (22) are given as follows:

$$W_i = \frac{1}{2}(1 - e^{Q_i d_i}) Q_i^{-2} S_i^T \qquad \text{Eq. (23)}$$

$$W_i^{[A](+)} = \frac{1}{2} d_i Q_i^{-2} S_i^T - Q_i^{-1} W_i \qquad \text{Eq. (24)}$$

-continued $$W_i^{[A](-)} = Q_i^{-1} W_i - \frac{1}{2} d_i e^{-Q_i d_i} Q_i^{-2} S_i^T \quad \text{Eq. (25)}$$

$$W_i^{(+)} = \frac{1}{2} d_i Q_i^{-2} S_i^T - Q_i^{-1} W_i \quad \text{Eq. (26)}$$

$$W_i^{[B](+)} = \frac{1}{2 \cdot 2!} d_i^2 Q_i^{-2} S_i^T - Q_i^{-1} W_i^{[A](+)} \quad \text{Eq. (27)}$$

$$W_i^{[B](-)} = Q_i^{-1} W_i^{[A](-)} - \frac{1}{2 \cdot 2!} d_i^2 e^{-Q_i d_i} Q_i^{-2} S_i^T. \quad \text{Eq. (29)}$$

Using the integral formulas in Eqs. (18), (19), $\Psi_A$ defined in Eq. (16), and $\Psi_B$ in Eq. (19), Eq. (13) can be expressed for l=0, ..., L−1, as $$\Psi(z_l) - \Psi^{[0]}(z_l) = \sum_{j=1}^{l} \Theta_{lj}^{(+)} V_j \Psi(z_j) + \sum_{j=0}^{l-1} \overline{\Theta}_l^{(+)} V_{j+1} \Psi(z_j) + \quad \text{Eq. (29)}$$

$$\sum_{j=0}^{l-2} \tilde{\Theta}_{lj}^{(+)} V_{j+2} \Psi(z_j) + \sum_{j=2}^{l+1} \hat{\Theta}_{lj}^{(+)} V_{j-1} \Psi(z_j) + \sum_{j=l+1}^{L} \Theta_{lj}^{(-)} V_j \Psi(z_j) +$$

$$\sum_{j=l}^{L-1} \overline{\Theta}_{lj}^{(-)} V_{j+1} \Psi(z_j) + \sum_{j=l-1}^{L-2} \tilde{\Theta}_{lj}^{(-)} V_{j+2} \Psi(z_j) + \sum_{j=l+2}^{L} \hat{\Theta}_{lj}^{(-)} V_{j-1} \Psi(z_j)$$

Although the index l in Eq. (29) can be even or odd, the concrete expressions of $\Theta_{lj}^{(\pm)}$, $\overline{\Theta}_{lj}^{(\pm)}$, $\tilde{\Theta}_{lj}^{(\pm)}$, $\hat{\Theta}_{lj}^{(\pm)}$, for even l and odd l are different. Moreover, all even columns of the matrices $\tilde{\Theta}_{lj}^{(\pm)}$ and $\hat{\Theta}_{lj}^{(\pm)}$ vanish. This is due to the properties of second-order expansion.

The discretized Lippmann-Schwinger equation for l=L, i.e., Eq. (14), is calculated as follows:

$$\Psi(z_L) - \Psi^{[0]}(z_L) = \sum_{j=1}^{L} \Theta_{Lj}^{(+)} V_j \Psi(z_j) + \quad \text{Eq. (30)}$$

$$\sum_{j=0}^{L-1} \overline{\Theta}_{Lj}^{(+)} V_{j+1} \Psi(z_j) + \sum_{j=0}^{L-2} \tilde{\Theta}_{Lj}^{(+)} V_{j+2} \Psi(z_j) + \sum_{j=2}^{L} \hat{\Theta}_{Lj}^{(+)} V_{j-1} \Psi(z_j)$$

When the number of layers L is an odd integer, it is first considered that one layer is added to the remaining (L−1) even layers, which include (L−1)/2 pairs. In this regards, an integration formula to be applied for the one added layer may be given depending on whether the added layer is considered to lie above a given pair or below a given pair. In general, it is possible that an M-th order interpolation is applied for each layer divided or each section partitioned from the virtual periodic structure.

Eqs. (29) and (30) can be consolidated in one expanded matrix form of a linear system of equations:

$$X = X^{[0]} + [GV + \overline{G}\overline{V} + \tilde{G}\tilde{V} + \hat{G}\hat{V}]X, \quad \text{Eq. (31)}$$

where X and $X^{[0]}$ are column vectors of dimension L+1 with the layer components $\Psi(z_l)$ and $\Psi^{[0]}(z_l)$, respectively. Each of the layer components $\Psi(z_l)$ and $\Psi^{[0]}(z_l)$ are still column vectors of dimension (2N+1) with the coupled-wave components. G, $\overline{G}$, $\tilde{G}$, $\hat{G}$ are square matrices with $(L+1)^2$ layer components, each layer component being $(2N+1)^2$ square matrices in coupled-wave space. The square matrices V, $\overline{V}$, $\tilde{V}$, $\hat{V}$ having $(L+1)^2$ layer components are essentially constructed from the perturbation potential $V(z_l)$ having components $(2N+1)^2$ in coupled-wave space.

Eq. (31) can be generalized for N th order interpolation as follows: in this case the number of matrix to be calculated increased by 2N.

$$X - X^{[0]} = \left[\sum_{i=1}^{2N} G_i V_i\right] X \quad \text{Eq. (32)}$$

Thus far, the calculation of TE mode quantities was considered; the calculation of TM mode quantities will be described below.

Due to the periodicity of the periodic structure in the x direction, the TM mode solutions to Maxwell's equation can be written as $$H_y(x, z) = \sum_{n=-\infty}^{\infty} \Phi_n(z) e^{ik_{xn} x}, \quad \text{Eq. (33)}$$

$$E_x(x, z) = -i \sqrt{\frac{\varepsilon_0}{\mu_0}} \frac{1}{k_0} \sum_{n=-\infty}^{\infty} \sum_{n'=-\infty}^{\infty} \varepsilon_{(n-n')}^{\#}(z) \partial_z \Phi_n(z) e^{ik_{xn} x}. \quad \text{Eq. (34)}$$

Herein, $\in_{(n-n')}^{\#}(z)$ is an expansion coefficient when the inverse of a dielectric function $\in(x,z)$ is expanded in Fourier series:

$$\frac{1}{\varepsilon(x, z)} = \sum_{h=-\infty}^{\infty} \varepsilon_h^{\#}(z) e^{-i2\pi h x/\Lambda} \quad \text{Eq. (35)}$$

From Maxwell's equations, the column vector $\Phi(z)$ (the projected-space wave vector) whose components are the expansion coefficients $\Phi_n(z)$ in Eq. (33) satisfy the following equation:

$$\left[\frac{d}{dz}\left(P(z) \frac{d\Phi(z)}{dz}\right) + k_0^2 I - KE(z)^{-1} K\right] \Phi(z) = 0, \quad \text{Eq. (36)}$$

where P(z) is a square matrix with the (n,n) element being equal to $\in_{(n-n')}^{\#}(z)$. Column vectors $\Phi^{[0]}(z)$ and $\Phi(z)$ whose components are the expansion coefficient functions (of z) in Eq. (38) for the zero-th order structure and the perturbed structure, respectively, satisfy the following Lippmann-Schwinger equation:

$$\Phi(z) - \Phi^{[0]}(z) = \quad \text{Eq. (37)}$$

$$-\int dz' \left[G(z, z') K \tilde{V}(z') K \Phi(z') + \frac{\partial G(z, z')}{\partial z'} V(z') \frac{\partial \Phi(z')}{\partial z'}\right],$$

where K is as defined in the TE mode, $\tilde{V}(z) = E(z)^{-1} - (E^{[0]})^{-1}(z)$, and $V(z) = P(z) - P^{[0]}(z)$. In Eq. (37), Li's factorization rule was used for a rapid convergence. The column vector $\Phi^{[0]}(z)$ and the Green function G(z,z') can be calculated basically in a similar way as in the TE mode.

That is, by setting $z \to z_{l-1}$ for z located inside the layer l (l=1, ..., L) and $z \to z_L$ for z located inside the layer L and by use of Eqs. (7) and (8), and assuming that the perturbation potentials $\tilde{V}(z')$ and $V(z')$ have constant values $\tilde{V}_j$ and $V_j$, respectively, Eq. (37) is discretized for l=1, ..., L−1 as follows:

$$\Phi(z_{l-1}) - \Phi^{[0]}(z_{l-1}) = \quad \text{Eq. (38)}$$

$$-\Bigg\{ S_l \Bigg[ (1+R_l) \sum_{j=1}^{l-1} \overline{T}_{l-1}\ldots\overline{T}_j \int_{z_{j-1}}^{z_j} dz' f_{jj}^+(z') K \tilde{V}_j K \Phi(z') +$$

$$(\overline{r}_l + 1) \int_{z_{l-1}}^{z_l} dz' g_{ll}^-(z') K \tilde{V}_l K \Phi(z') +$$

$$(\overline{r}_l + 1) \sum_{j=l+1}^{L} \overline{I}_l \ldots \overline{I}_{j-1} \int_{z_{j-1}}^{z_j} dz' g_{jj}^-(z') K \tilde{V}_j K \Phi(z') \Bigg] +$$

$$S_l \Bigg[ (1+R_l) \sum_{j=1}^{l-1} \overline{T}_{l-1}\ldots\overline{T}_j \int_{z_{j-1}}^{z_j} dz' (f_{jj}^+)'(z') V_j \Phi'(z_j) +$$

$$(\overline{r}_l + 1) \int_{z_{l-1}}^{z_l} dz' (g_{ll}^-)'(z') V_l \Phi'(z_j) +$$

$$(\overline{r}_l + 1) \sum_{j=l+1}^{L} \overline{I}_l \ldots \overline{I}_{j-1} \int_{z_{j-1}}^{z_j} dz' (g_{jj}^-)'(z') V_j \Phi'(z_j) \Bigg] \Bigg\}.$$

Meanwhile, for l=L, Eq. (37) becomes $$\Phi(z_L) - \Phi^{[0]}(z_L) = \quad \text{Eq. (39)}$$

$$-\Bigg\{ S_L(e^{-Q_L d_L} + e^{Q_L d_L} R_L) \Bigg[ \sum_{j=1}^{L-1} \overline{T}_{L-1}\ldots\overline{T}_j \int_{z_{j-1}}^{z_j} dz' f_{jj}^+(z') K$$

$$\tilde{V}_j K \Phi(z') \int_{z_{L-1}}^{z_L} dz' f_{LL}^+(z') K \tilde{V}_L K \Phi(z') \Bigg] +$$

$$S_L(e^{-Q_L d_L} + e^{Q_L d_L} R_L)$$

$$\Bigg[ \sum_{j=1}^{L-1} \overline{T}_{L-1}\ldots\overline{T}_j \int_{z_{j-1}}^{z_j} dz' (f_{jj}^+)'(z') V_j \Phi'(z') +$$

$$\int_{z_{L-1}}^{z_L} dz' (f_{LL}^+)'(z') V_L \Phi'(z') \Bigg] \Bigg\}$$

To enhance accuracy, similar to Eq. (15), the integrals with $K\tilde{V}_j K$ instead of $V_j$ in Eqs. (18) and (19) is obtained by using the second-order interpolation for the projected-space perturbed wave $\Phi(z)$, and analytic integrations are carried out for second part of the integrand in Eq. 37, and finally we can obtain the following Eqs. (40) and (41). In a similar way as in the TE mode TE mode, II and IP $\Psi(z_{j-1})$ are used for even-numbered layers, and I and $\Psi(z_j)$ for odd-numbered layers.

$$\int_{z_{j-1}}^{z_j} dz' \partial_{z'} f_{jj}^+(z') V_j \partial_{z'} \Psi_{II}(z') = \quad \text{Eq. (40)}$$

$$G_j^{[2](+)} V_j \Psi(z_{j-1}) + G_j^{[2][B](II)(+)} V_j \Psi(z_{j-1})$$

$$\int_{z_{j-1}}^{z_j} dz' \partial_{z'} f_{jj}^+(z') V_j \partial_{z'} \Psi_I(z') =$$

$$G_j^{[2](+)} V_j \Psi(z_j) + G_j^{[2][B](I)(+)} V_j \Psi(z_j)$$

$$\int_{z_{j-1}}^{z_j} dz' \partial_{z'} g_{jj}^-(z') V_j \partial_{z'} \Psi_{II}(z') = \quad \text{Eq. (41)}$$

$$G_j^{[2](-)} V_j \Psi(z_{j-1}) + G_j^{[2][B](II)(-)} V_j \Psi(z_{j-1})$$

$$\int_{z_{j-1}}^{z_j} dz' \partial_{z'} g_{jj}^-(z') V_j \partial_{z'} \Psi_I(z') =$$

$$G_j^{[2](-)} V_j \Psi(z_j) + G_j^{[2][B](I)(-)} V_j \Psi(z_j)$$

where $$\begin{pmatrix} G^{[2](+)} \\ G^{[2](-)} \end{pmatrix}_j = \begin{pmatrix} (1 + \overline{r}uR)e^{Qd} - \overline{r}u \\ uRe^{Qd} - u \end{pmatrix}_j Q_j W_j \quad \text{Eq. (42)}$$

$$\begin{pmatrix} G^{[A][I](+)} \\ G^{[A][I](-)} \end{pmatrix}_j = \begin{pmatrix} -(1+\overline{r}uR)e^{Qd}QW^{[A](+)} + \overline{r}uQW^{[A](-)} \\ -uRe^{Qd}QW^{[A](+)} + uQW^{[A](-)} \end{pmatrix}_j \quad \text{Eq. (43)}$$

$$\begin{pmatrix} G^{[A][II](+)} \\ G^{[A][II](-)} \end{pmatrix}_j = \begin{pmatrix} (1+\overline{r}uR)e^{Qd}QW^{[A](+)} + \overline{r}uQW^{[A](-)} \\ uRe^{Qd}QW^{[A](+)} + uQW^{[A](-)} \end{pmatrix}_j \quad \text{Eq. (44)}$$

With these integration formulas. Eq. (38) is eventually calculated as follows:

$$\Phi(z_L) - \Phi^{[0]}(z_L) = \sum_{j=1}^{l} [\Theta_{lj}^{(+)} K V_j K + \Delta_{lj}^{(+)} V_j]\Phi(z_j) + \quad \text{Eq. (45)}$$

$$\sum_{j=0}^{l-1} [\overline{\Theta}_{lj}^{(+)} K V_{j+1} K + \overline{\Delta}_{lj}^{(+)} V_{j+1}]\Phi(z_j) +$$

$$\sum_{j=0}^{l-2} [\tilde{\Theta}_{lj}^{(+)} K V_{j+2} K + \tilde{\Delta}_{lj}^{(+)} V_{j+2}]\Phi(z_j) +$$

$$\sum_{j=2}^{l+1} [\hat{\Theta}_{lj}^{(+)} K V_{j-1} K + \hat{\Delta}_{lj}^{(+)} V_{j-1}]\Phi(z_j) +$$

$$\sum_{j=l+1}^{L} [\Theta_{lj}^{(-)} K V_j K + \Delta_{lj}^{(-)} V_j]\Phi(z_j) +$$

$$\sum_{j=l}^{L-1} [\overline{\Theta}_{lj}^{(-)} K V_{j+1} K + \overline{\Delta}_{lj}^{(-)} V_{j+1}]\Phi(z_j) +$$

$$\sum_{j=l-1}^{L-2} [\tilde{\Theta}_{lj}^{(-)} K V_{j+2} K + \tilde{\Delta}_{lj}^{(-)} V_{j+2}]\Phi(z_j) +$$

$$\sum_{j=l+2}^{L} [\hat{\Theta}_{lj}^{(-)} K V_{j-1} K + \hat{\Delta}_{lj}^{(-)} V_{j-1}]\Phi(z_j)$$

where the concrete forms of $\Delta_{lj}^{(\pm)}$, $\overline{\Delta}_{lj}^{(\pm)}$, $\tilde{\Delta}_{lj}^{(\pm)}$, $\hat{\Delta}_{lj}^{(\pm)}$, are different for even l and odd l. Meanwhile, for l=L, Eq. (39) becomes $$\Phi(z_L) - \Phi^{[0]}(z_L) = \sum_{j=1}^{L} [\Theta_{Lj}^{(+)} K V_j K + \Delta_{Lj}^{(+)} V_j]\Phi(z_j) + \quad \text{Eq. (46)}$$

$$\sum_{j=0}^{L-1} [\overline{\Theta}_{Lj}^{(+)} K V_{j+1} K + \overline{\Delta}_{Lj}^{(+)} V_{j+1}]\Phi(z_j) +$$

$$\sum_{j=0}^{L-2} [\tilde{\Theta}_{Lj}^{(+)} K V_{j+2} K + \tilde{\Delta}_{Lj}^{(+)} V_{j+2}]\Phi(z_j) + \sum_{j=2}^{L} \hat{\Theta}_{Lj}^{(+)} K V_{j-1} \Psi(z_j)$$

In the case of odd L, as in the TE mode, by considering that one layer is added to (L−1) layers, the second-order interpolation method can be applied. Similarly to the TE mode calculation, a system of linear equations for the discretized projected-space perturbed magnetic field $\Phi(z_l)$ in the TM mode can be obtained as follows:

$$X = X^{[0]} + [GV' + \overline{G}\overline{V}' + \tilde{G}\tilde{V}' + \hat{G}\hat{V}' + HV + \overline{H}\overline{V} + \tilde{H}\tilde{V} + \hat{H}\hat{V}]X, \quad \text{Eq. (47)}$$

to where $\Phi(z_l)$ and $\Phi^{[0]}(z_l)$ are column vectors of dimension L+1 with layer components $\Phi(z_l)$ and $\Phi^{[0]}(z_l)$, respectively, still being column vectors of dimension (2L+1) with coupled-wave basis components. G, $\overline{G}$, $\tilde{G}$, $\hat{G}$ are as defined in TE mode. H, $\overline{H}$, $\tilde{H}$, $\hat{H}$ are square matrices with (L+1)² layer components, each layer component being square matrices with (2L+1)² components on a coupled-wave basis, and the square matrices V, $\overline{V}$, $\tilde{V}$, $\hat{V}$ having (L+1)² layer components are essentially constructed from the perturbation potential $V(z_l)$ having components (2L+1)² in coupled-wave space.

Once the layer components of the TE mode electric field $\Psi(z_l)$ and the TM mode magnetic field $\Phi(z_l)$ are determined, the reflectance or transmittance of the virtual periodic structure (200b) illustrated in FIGS. 6 and 7 can be calculated by the method described in Korean Patent No. 10-0892486.

The above-described calculated reflectance or transmittance of each of the TE mode and the TM mode is compared with the measured reflectance or transmittance. The comparison results can be applied to the nondestructive analysis of various periodic structures, for example, holographic grating structures, surface relief and multilayer grating structures, plane dielectric or absorptive holographic grating structures, random sectional dielectric and absorptive surface relief grating structures, two-dimensional surface relief grating structures, and anisotropic grating structures. It is to be understood that the scope of the invention is not limited to the disclosed embodiments.

Figure 8:
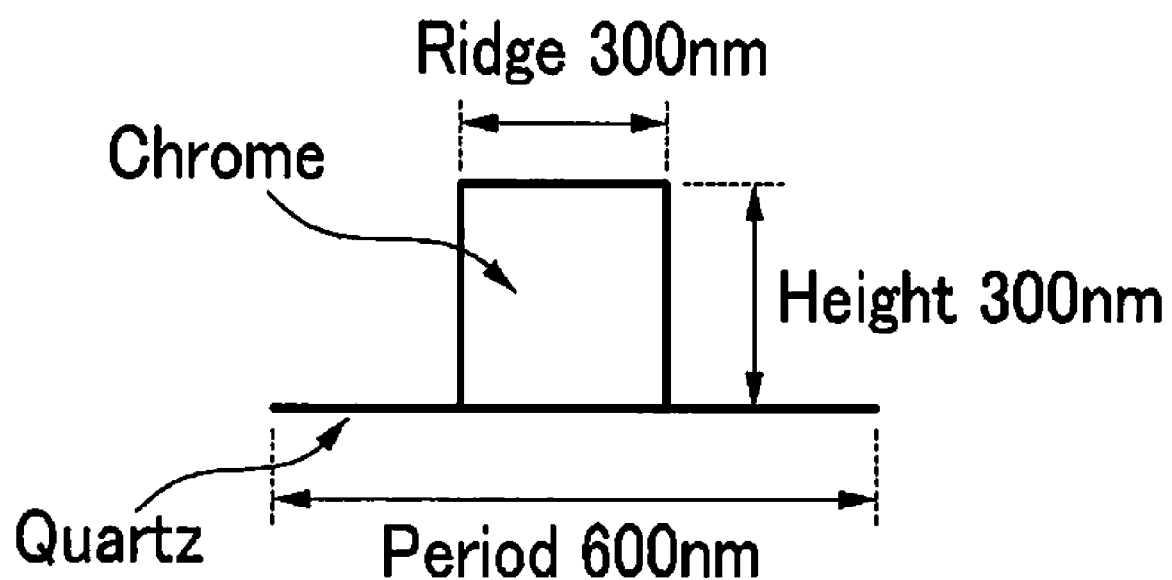
FIG. 8 is a sectional view of the geometrical formation of an exemplary virtual periodic structure according to an embodiment of the present invention.

Comparison of Computation Time with Green Function Method with the First-Order Interpolation With a periodic structure illustrated in FIG. 8, accuracy can be investigated. FIG. 8 is a sectional view of the geometrical formation of an exemplary virtual periodic structure in accordance with an embodiment of the present invention. FIGS. 9 to 12 are graphs illustrating results from the principal order reflectance of a virtual periodic structure calculated by the RCWA method, the Green function method with the first-order interpolation, and a method according to the present invention, i.e., the Green function method with the second-order interpolation.

The ridge region (stacked on a quartz substrate) of the periodic structure illustrated in FIG. 8 is composed of a single substance of chromium. The period $\Lambda$ of the periodic structure is 600 nm, and the width and depth of the chromium ridge are both 300 nm. FIGS. 9 to 14 are graphs illustrating results from the principal order reflectance of a virtual periodic structure calculated by the RCWA, the Green function method with the first-order interpolation, and a method according to an embodiment of the present invention.

FIGS. 9 to 14 are to examine the accuracy in accordance with an embodiment of the present invention, and the reference data for comparison in FIGS. 9 to 14 was obtained from a simulation by the RCWA method with the number of Fourier components N=81 which is large enough for the test sample of FIG. 8. What is compared in the present example is the difference in computation speed between the calculation by the existing Green function method based on the linear interpolation and that by the embodiment of the present invention. This comparison, on one hand, should be done under the same accuracy conditions.

On the other hand, this comparison is also possible by comparing accuracy under the same layer number condition, for enhancement of computation speed by deducing the number of layers, at the same time, is accompanied by a larger error. Therefore, in order to see that the method by the embodiment of the present invention provides better methodology, the error will be compared below. Ellipsometric method is chosen as a typical example among various optical measurement methods. Therefore, the error formula used for comparison is given as:

$$\text{error} = \frac{1}{2N} \sum_{i=1}^{2N} \left(\frac{\psi_s - \psi_\varepsilon}{\psi_\varepsilon}\right)^2, \quad \text{Eq. (48)}$$

where $\Psi_S$ denotes the values of $\Psi$ and $\Delta$ in ellipsometry obtained from the simulation by the Green function method and $\Psi_\varepsilon$ denotes those obtained by the RCWA method with high precision.

Figure 9:
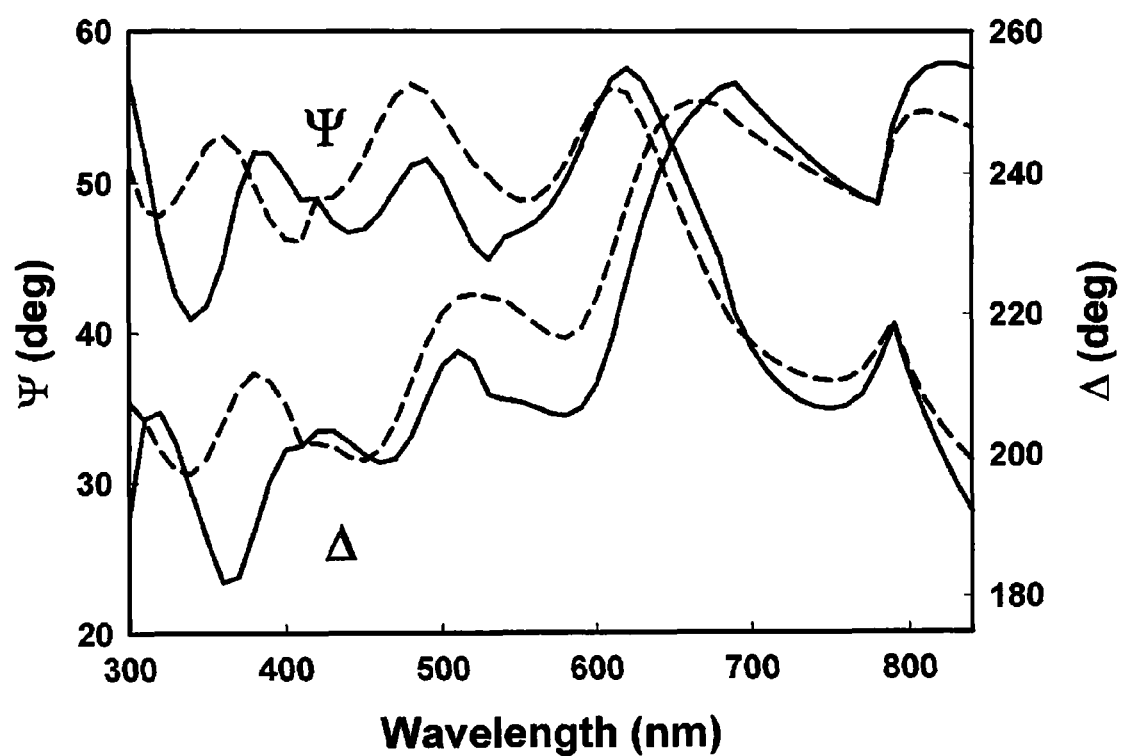
FIGS. 9 to 14 are graphs illustrating results from principal order reflectance of a virtual periodic structure calculated by the RCWA method, the Green function method with first order interpolation, and a method according to an embodiment of the present invention, i.e., the Green function method with second order interpolation.
Figure 10:
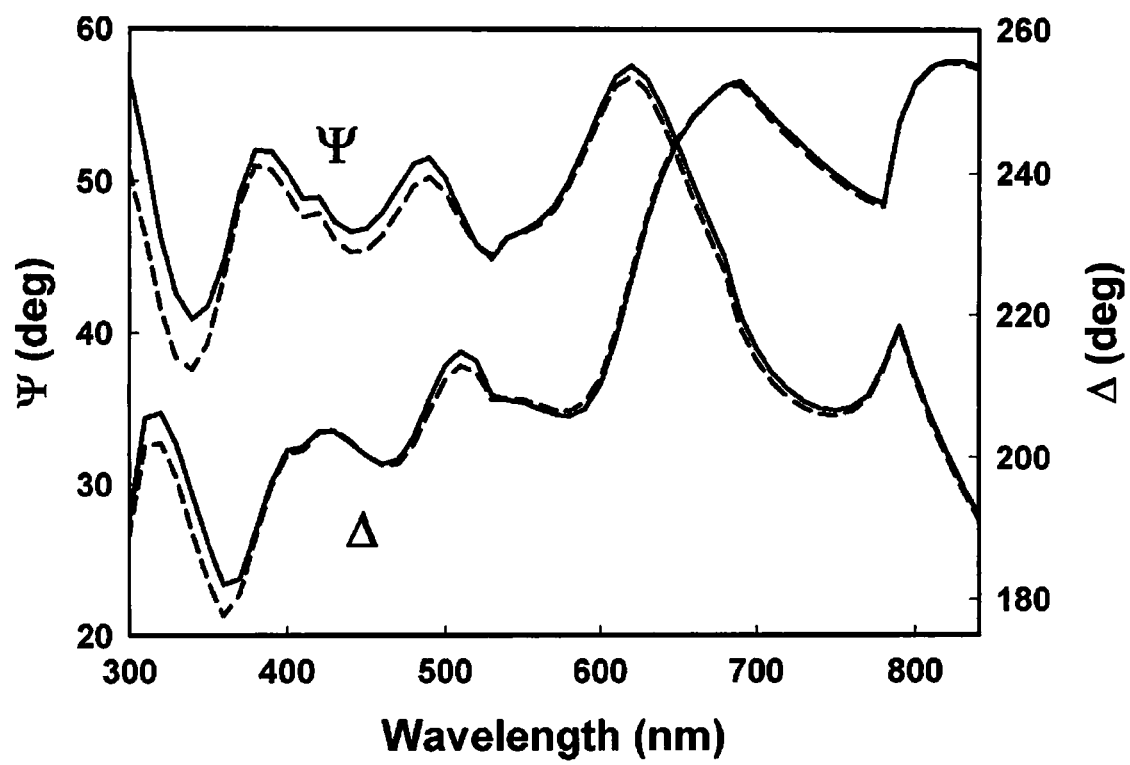

First, through FIGS. 9 and 10, the comparison of results by the existing Green function method and by the embodiment of the present invention is examined.

FIGS. 9 and 10 show the result of calculations with 10 divided layers as for the structure illustrated in FIG. 8. The solid lines denote the values for the corresponding quantities calculated by the RCWA method with high precision, the dotted lines in FIG. 9 denote the graphs of $\Psi$ and $\Delta$ with respect to wavelength by the existing Green function method, and the dotted lines in FIG. 10 denote those by the embodiment of the present invention.

As may be seen in FIG. 9, a significant difference is found between the calculations by the existing Green function method and the RCWA method with high precision. The error calculated using Eq. (48) was 4.7834E-3.

On the contrary, as may be seen in FIG. 10, the difference between the calculations by the embodiment of the present invention and the RCWA method with high precision becomes smaller. The error was 6.4878E-4, which is a reduced by one order of magnitude.

As a consequence, in accordance with the embodiment of the present invention, the calculated values by the second-order-interpolated Green function method, with a small number of divided layers and a small error, approach the real values.

Figure 11:
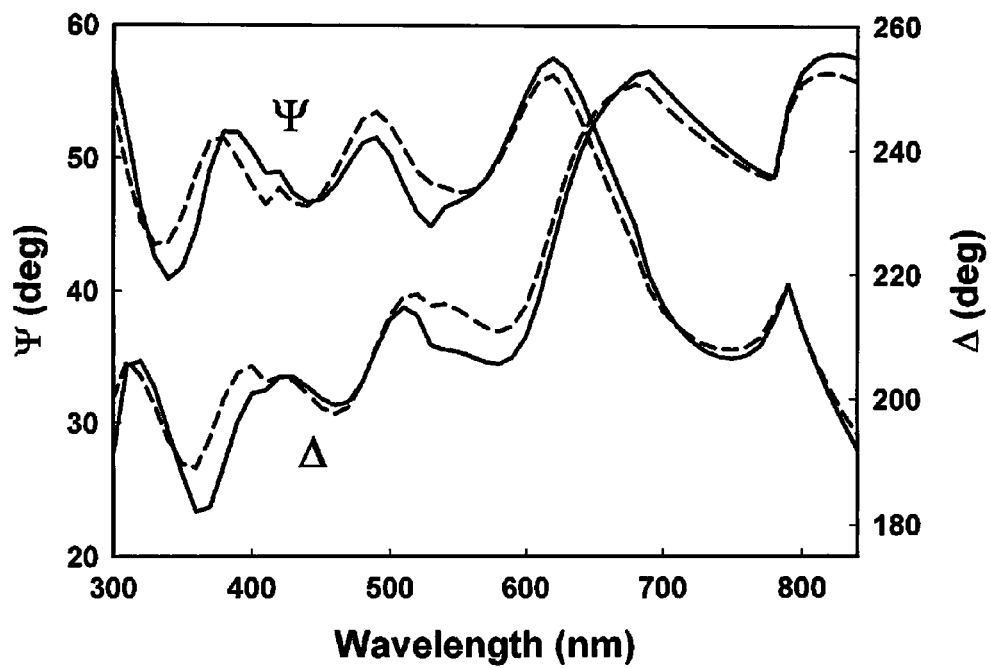
Figure 12:
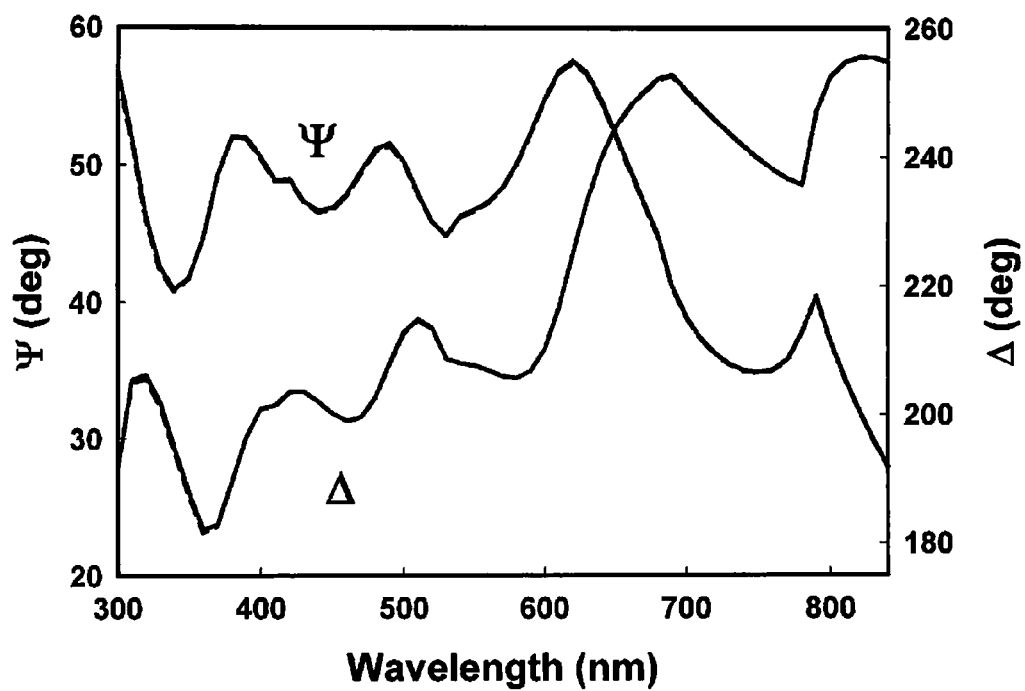

Using FIGS. 11 and 12, the results of the existing Green function method and by the embodiment of the present invention are compared again.

Differently from FIGS. 9 and 10, FIGS. 10 and 11 show the result of calculations with 20 divided layers as for the structure illustrated in FIG. 8. As in FIGS. 9 and 10, the solid lines denote the values calculated by the RCWA method with high precision, the dotted lines in FIG. 11 denote the graphs of $\Psi$ and $\Delta$ with respect to wavelength by the existing Green function method, and the dotted lines in FIG. 12 denote those by the embodiment of the present invention, which is the second-order-interpolated Green function method.

The existing Green function method, of course, reduced the error when the number of the divided layers was changed to 20 from 10, as may be seen in FIG. 11. In this case, the error was calculated as 8.618E-4.

On the contrary, when the number of the divided layers L was 20, the embodiment of the present invention gave almost the same results as the RCWA calculation, as may be seen in FIG. 12. The error obtained using Eq. (55) was 5.3909E-6. That is, with the same number of layers, the embodiment of the present invention yielded a significantly improved error value by a factor of 100.

To reach the same error value as in FIG. 12 with the existing Green function method, the periodic structure in FIG. 8 should be divided into 85 layers. The comparison of the computation time under the same error condition was 32.8 (existing Green function method):1.5 (embodiment of present invention). Therefore, in accordance with an embodiment of the present invention, in calculations in which a prescribed error should demanded, the Green function method with the second order interpolation is more efficient than the existing Green function method.

Figure 13:
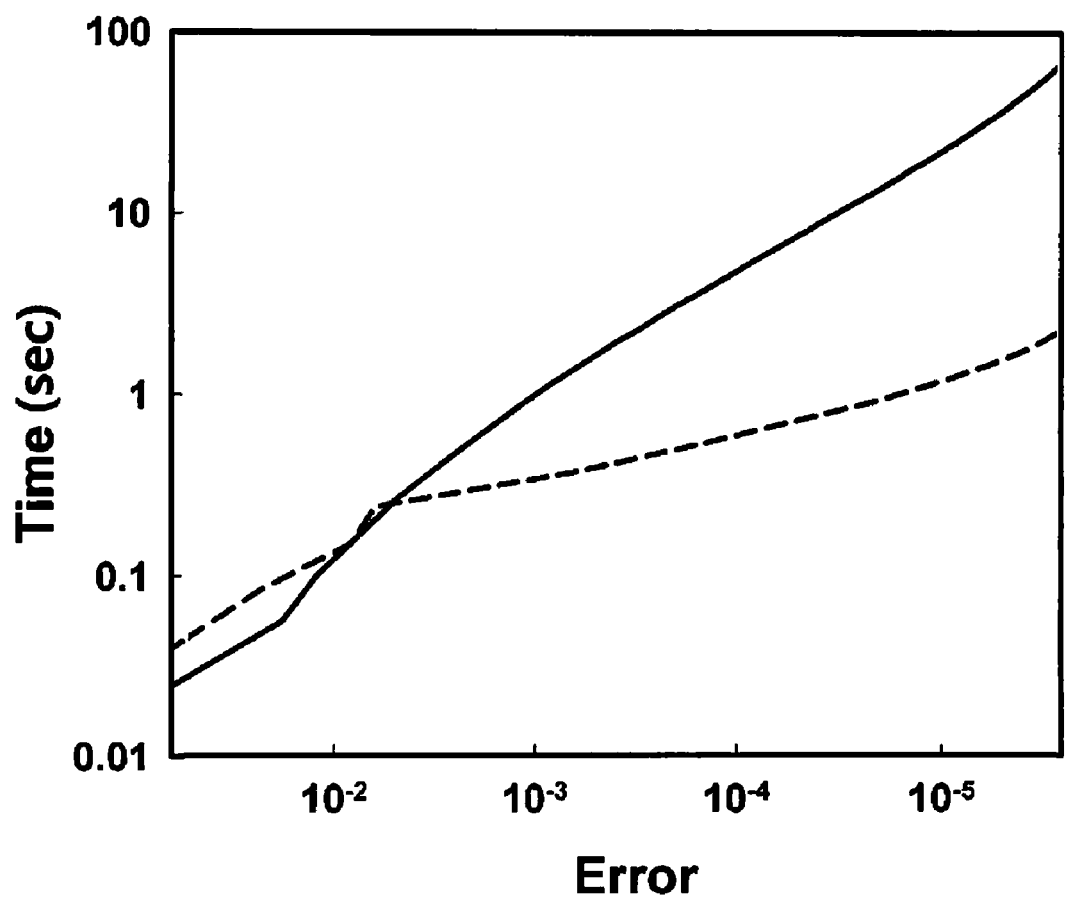
Figure 14:
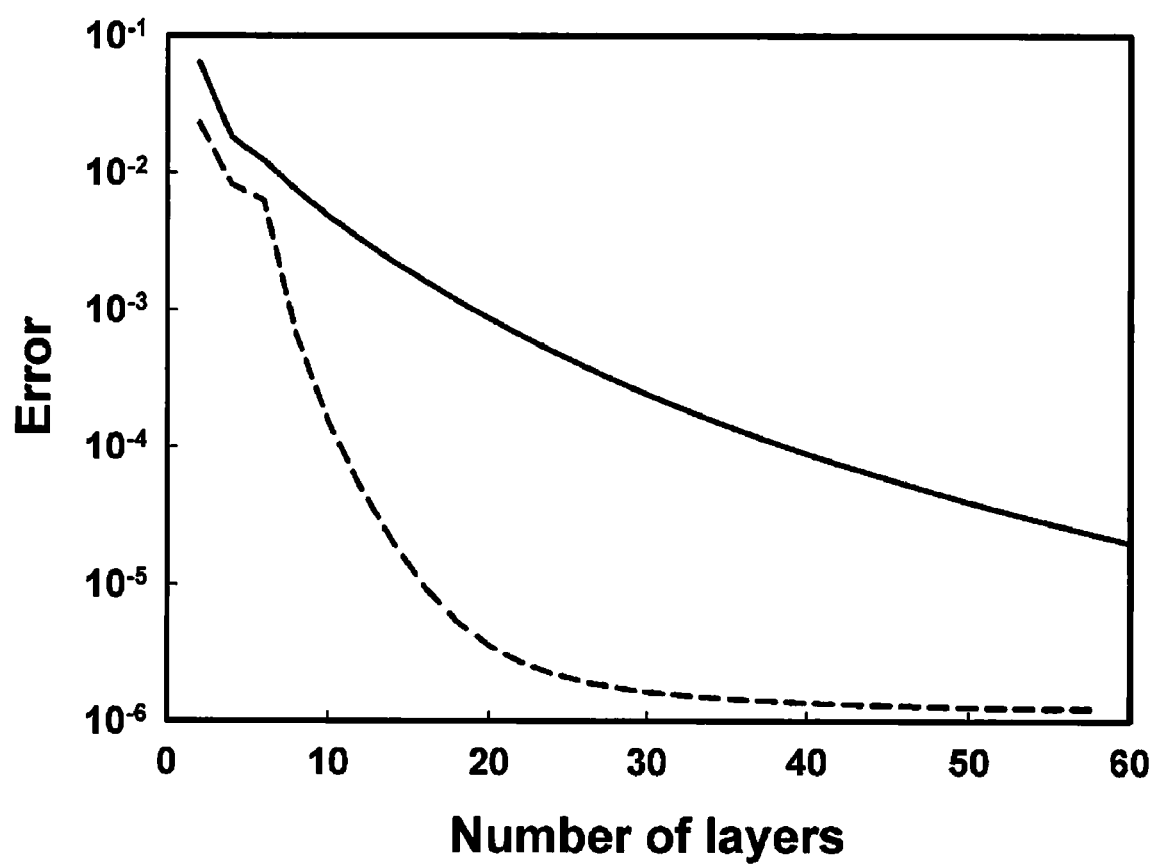

This point is illustrated in FIGS. 13 and 14 in more detail.

The x-axis and y-axis in FIG. 13 denote error and elapsed time, respectively. In FIG. 14, the x-axis and y-axis denote the number of divided layers and the ratio of error, respectively. In FIGS. 13 and 14, the solid line is for the existing Green function method and the dotted line is for the embodiment of the present invention.

In the case in which the number of layers is small, the elapsed time by the embodiment of the present invention is longer than for the existing Green function method.

However, because it is meaningless to only reduce time without an investigation of accuracy, it is desirable to compare the computation time under the same error condition. As can be seen in FIG. 13, if the allowable error is 1.00E-5, which is generally accepted, the Green function method in accordance with the embodiment of the present invention has a merit of significantly reducing the computation time in the calculation with the same error.

Meanwhile, in FIG. 14, because the calculation by the embodiment of the present invention allows a small number of divided layers in a case where the same ratio of error is required, another advantage is realized of having fewer added terms relative to the existing Green function method.

Putting this together, compared with the existing Green function method, the embodiment of the present invention has sufficient accuracy in calculation even with a small number of layers, and reduces the elapsed time significantly in calculation with the same error. Therefore, it can be used for in-situ monitoring in a real manufacturing process.

The invention has been described using preferred exemplary embodiments. However, it is to be understood that the scope of the invention is not limited to the disclosed embodiments. On the contrary, the scope of the invention is intended to include various modifications and alternative arrangements within the capabilities of persons skilled in the art using presently known or future technologies and equivalents. The scope of the claims, to therefore, should be accorded the broadest interpretation so as to encompass all such modifications and similar arrangements.

What is claimed is:

1. A nondestructive analysis for a periodic structure, comprising steps of:
   (a) illuminating a real periodic structure and measuring, by a detector, at least one physical property related to reflectivity or transmittance of the real periodic structure in response to the illumination;
   (b) calculating, by a processor, at least one physical property related to at least one of reflectivity or transmittance of a virtual periodic structure in response to the illumination,
   by setting the virtual periodic structure having a repeated shape, one-dimensionally, two-dimensionally or three-dimensionally and at least a horizontally repeating period,
   by dividing the virtual periodic structure into vertically stacked N layers,
   by defining a zero-th order structure and a perturbed structure from the virtual periodic structure, said perturbed structure being obtained by geometrically or physically changing the zero-th order periodic structure in a perturbation region,
   by calculating the zero-th order reflected or transmitted wave when light is incident on the zero-th order structure,
   by discretizing the Lippmann-Schwinger equation using M-th order interpolation with at least one divided layer of the virtual periodic structure, wherein $2 \leq M \leq N$,
   by calculating the perturbed reflected or transmitted wave from the discretized Lippmann-Schwinger equation, and
   by calculating the perturbed reflectivity or transmittance from the zero-th order reflected or transmitted wave and the perturbed reflected or transmitted wave; and
   (c) comparing the at least one physical property related to the reflectivity or the transmittance being measured in the step (a) with the corresponding at least one physical property related to the at least one of reflectivity or transmittance being calculated in the step (b);
   wherein the step (b) further comprises steps of:
   partitioning the N layers of the virtual periodic structure into X sections, wherein $1 \leq X \leq (N-1)$, and
   discretizing the Lippmann-Schwinger equation using Mi-th order interpolation with the partitioned sections wherein $1 \leq Mi \leq N$.

2. The method of claim 1, wherein at least one of the partitioned sections has different number of layer from other sections.

3. The method of claim 1, wherein the reflectivity or transmittance is that of other detectable diffraction orders as well as the zero-th order.

4. The method of claim 1, wherein the surface of virtual periodic structure has a substance outside the layer, said substance being a gaseous, liquid, or solid phase.

5. The method of claim 1, wherein the virtual periodic structure is allowed to have at least one surface layer, and the surface layer includes at least one of a layer selected from the group consisting of an oxide layer, a coating layer, or a surface roughness layer.

6. The method of claim 1, wherein the physical properties are related to amplitude or phase of a reflected wave or a transmitted wave of an incident wave.

7. The method of claim 1, wherein the step (b) further comprises steps of:
   expanding perturbation potential in each divided layer in a Fourier series; and
   applying the M-th order interpolation formula for the perturbed wave to the reflected or transmitted wave in each divided layer separately according to the layer index.

8. The method of claim 1, wherein the virtual periodic structure is divided into N layers with at least two different heights.

9. The method of claim 1, wherein comparing includes comparing, by a processor, the at least one physical property related to the reflectivity or the transmittance being measured in the step (a) with the corresponding at least one physical property related to the at least one of reflectivity or transmittance being calculated in the step (b).

* * * * *